(12) United States Patent
Heisig et al.

(10) Patent No.: US 9,089,129 B2
(45) Date of Patent: Jul. 28, 2015

(54) NON-AEROSOL FOAMING ALCOHOL HAND SANITIZER

(71) Applicant: AMERICAN STERILIZER COMPANY, Mentor, OH (US)

(72) Inventors: Christopher C. Heisig, Saint Louis, MO (US); Nancy-Hope E. Kaiser, Pontoon Beach, IL (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 55 days.

(21) Appl. No.: 13/644,677

(22) Filed: Oct. 4, 2012

(65) Prior Publication Data

US 2013/0090380 A1    Apr. 11, 2013

Related U.S. Application Data

(60) Provisional application No. 61/544,802, filed on Oct. 7, 2011.

(51) Int. Cl.

| | |
|---|---|
| *A01N 33/04* | (2006.01) |
| *A01P 1/00* | (2006.01) |
| *A01N 41/02* | (2006.01) |
| *A01N 31/02* | (2006.01) |
| *A01N 25/16* | (2006.01) |

(52) U.S. Cl.
CPC ............. *A01N 31/02* (2013.01); *A01N 25/16* (2013.01)

(58) Field of Classification Search
CPC .. C07D 413/04; C07D 471/06; C07D 471/08; C07D 471/10; C07D 491/052; C07D 491/107; C07D 498/06; C07D 513/04; C07D 207/452; C07D 209/02; C07D 209/08; C07D 209/12; C07D 209/14; C07D 209/18
USPC .................................. 514/517, 642
See application file for complete search history.

(56) References Cited

U.S. PATENT DOCUMENTS

| | | |
|---|---|---|
| 5,607,980 A | 3/1997 | McAtee et al. |
| 5,951,993 A | 9/1999 | Scholz et al. |
| 6,352,701 B1 | 3/2002 | Scholz et al. |
| 6,423,239 B1 | 7/2002 | Cathey et al. |
| 6,562,360 B2 | 5/2003 | Scholz et al. |
| 6,610,315 B2 | 8/2003 | Scholz et al. |
| 7,186,416 B2 | 3/2007 | Popp et al. |
| 7,268,165 B2 | 9/2007 | Greten et al. |
| 7,468,384 B2 * | 12/2008 | Levy et al. ..................... 514/373 |
| 7,651,990 B2 | 1/2010 | Asmus |
| 7,670,615 B2 | 3/2010 | Veeger et al. |
| 7,683,018 B2 | 3/2010 | Koivisto et al. |
| 7,723,279 B2 | 5/2010 | Lestage et al. |
| 7,842,725 B2 | 11/2010 | Wegner et al. |
| 7,985,773 B2 | 7/2011 | Greten et al. |
| 8,053,399 B2 | 11/2011 | Seidling et al. |
| 8,124,115 B2 | 2/2012 | Veeger et al. |
| 8,263,098 B2 | 9/2012 | Fernandez de Castro et al. |
| 2003/0069317 A1 | 4/2003 | Seitz, Jr. et al. |
| 2006/0039942 A1 | 2/2006 | Greten et al. |
| 2006/0275218 A1 | 12/2006 | Tamarkin et al. |
| 2007/0065383 A1 | 3/2007 | Fernandez de Castro et al. |
| 2009/0098067 A1 * | 4/2009 | Seidling et al. ................. 424/59 |
| 2009/0226498 A1 | 9/2009 | Flugge-Berendes et al. |
| 2009/0326076 A1 | 12/2009 | Asmus |
| 2010/0234475 A1 * | 9/2010 | Wegner et al. ................ 514/724 |
| 2011/0206630 A1 | 8/2011 | Rude |

FOREIGN PATENT DOCUMENTS

| | | |
|---|---|---|
| EP | 2216010 A1 | 8/2010 |
| WO | WO 2010/089228 A1 * | 8/2010 |

OTHER PUBLICATIONS

International Search Report and Written Opinion of the International Searching Authority; International application No. PCT/US12/58892; International filing date Oct. 5, 2012.
Paulson, D., et al., A Close Look at Alcohol Gel as an Antimicrobial Sanitizing Agent, AJIC, vol. 27, No. 4, pp. 332-338, 1999.

* cited by examiner

*Primary Examiner* — Melenie McCormick
*Assistant Examiner* — Taina D Matos Negron
(74) *Attorney, Agent, or Firm* — Hadak, Shunk & Farine Co. LPA

(57) ABSTRACT

A non-aerosol, foaming high alcohol content hand sanitizer is provided which has excellent antimicrobial activity and tolerance for organic load and excellent residual activity, as well as enhanced moisturization and skin-feel properties over currently marketed alcohol-based sanitizers. The inventive composition achieves an unexpectedly large amount of quality, stable foam even in the presence of significant quantities of skin conditioning agents through the use of novel silicone surfactants and achieves enhanced and prolonged antimicrobial efficacy through the combination of high alcohol content and activity enhancing components.

8 Claims, 5 Drawing Sheets

NON-AEROSOL FOAMING ALCOHOL HAND SANITIZER

FIELD OF THE INVENTION

This invention is directed to alcohol-based hand sanitizers, in particular to non-aerosol foaming hand sanitizers having high alcohol content, enhanced and prolonged antimicrobial efficacy and tolerance for organic loads and dilution, and excellent residual activity. The invention is also directed to a foaming, high alcohol content hand sanitizer having superior moisturization and aesthetic skin feel properties.

BACKGROUND OF THE INVENTION

Hand sanitizing products, including those that are alcohol-based, are known in the art. The use of alcohol-based hand sanitizing products, in particular, continues to grow, both within the United States and internationally. Alcohol-based sanitizers can be found in hospitals and other healthcare environments, the workplace, and in everyday home use. These products are considered especially useful when microbial contamination is a concern, particular in high risk areas of hospitals and prior to surgical procedures.

Some examples of high alcohol content sanitizers include U.S. Pat. No. 6,723,689, which describes an emollient antimicrobial composition comprising high alcohol content (60-95 wt. %), preservatives, a cationic cellulose polymer thickening agent, and silicone-based moisturizers and emollients, useful as a hand healthcare preparation or a pre-surgical scrub; U.S. Pat. Nos. 6,610,315; 6,562,360; 6,352,701 and 5,951,993, which describe alcohol compositions useful as pre-surgical scrub replacements or as a lotion or other hand preparation, comprising alcohol and a non-polymeric thickener system that includes mixtures of at least two emulsifiers; and U.S. Pat. No. 6,423,239, which describes a gel product for use as a skin sanitizer having a higher alcohol content and comprising, humectants, silicones as detackifying agents, moisturizers, and thickeners.

Alcohol and alcohol gels in which alcohol levels exceed about 50% have the most pronounced immediate antimicrobial effects; however, they lack persistent antimicrobial properties, i.e., residual activity or effect. Although alcohol may kill microbes on contact, upon drying, there is no means for killing or controlling microbial growth. As such, sanitizers using alcohol alone are often less effective over time. Hence, some alcohol-based compositions utilize additional antimicrobial compounds, which may themselves cause skin irritation and sensitization.

In addition, many alcohol-based products comprise thickening agents or emollients that increase the viscosity of the composition, in order to lower the alcohol evaporation rate and increase the exposure time that the alcohol is present on the skin. These thickened compositions often result in a less than optimal aesthetic skin feel in use or upon rinsing. Prolonged contact of high alcohol content may also dry and irritate the skin, and thickeners may trap dead skin and bacteria on the surface of the skin.

Alcohol-based antimicrobial compositions that provide prolonged and enhanced activity against various microorganisms without the need for additional antimicrobial agents have been described in the art. For example, U.S. Pat. Nos. 7,268,165 B2 and 7,985,773 82 (both to Greten et al., STERIS Corporation) describe antimicrobial compositions comprising a synergistic combination of a simple aliphatic alcohol and an activity enhancing substance (an aromatic alcohol or cationic substrate binding compound) that provides unexpected and persistent activity against a broad range of microorganisms, while, at the same time, moisturizing the skin. While additional antimicrobials may be added as an option, they are not required in order to provide enhanced and prolonged antimicrobial effect. The Greten et al. compositions are stated to be useful as hand sanitizers or pre-surgical scrubs, but are not foaming compositions.

Foaming alcohol sanitizers have been commercially available for many years, especially in healthcare settings. Traditionally, most foaming alcohol sanitizers used propellant-based, i.e., aerosol, technologies to create and stabilize foam, and these products are still widely used in this market. However, due to recent concerns about disposal of propellant systems, environmental sustainability, various safety issues, and regulatory scrutiny, non-aerosol, alcohol-based products have recently found their way into the market as replacements for aerosol products.

Most non-aerosol, alcohol-based foaming hand sanitizers utilize either fluorosurfactant or linear silicone surfactant chemistries to lower the surface tension of the alcohol system to a level that creates foam in an alcohol-rich environment. Most of these products have poor moisturization and aesthetic properties, when dispensed through an appropriate dispenser (mechanical). By way of example, U.S. Pat. No. 7,723,279 describes a foaming non-aerosol, alcohol-based composition comprising polymeric fluorosurfactants as foaming agents; and U.S. Pat. No. 7,683,018 describes a foaming non-aerosol, alcohol-based composition comprising anionic phosphate fluorosurfactants as the primary foaming agent. Other compositions are commercially available that utilize fluorinated surface active agents.

Other non-aerosol, alcohol-based compositions utilize silicone-based compounds either as the sole foaming surfactant or in conjunction with fluorosurfactants or other surfactants. Some examples include: U.S. Pat. No. 8,053,399, which discloses a foaming composition containing very little water that comprises the dimethicone copolyols PEG-10 dimethicone, PEG-12 dimethicone, or mixtures thereof; U.S. Pat. No. 7,670,615 (polysiloxane-polyether copolymers, such as, for example, a bis PEG-PPG-20/20 dimethicone); U.S. Pat. No. 7,651,990 (dimethicones and dimethicone copolyals with PEO and PPO side chains); U.S. Pat. No. 7,186,416 (polyoxyethylene ethers, esters, fatty acids, sulfated acids, sulfosuccinates, polysiloxane, sorbitan fatty acid esters, polyoxamers, and the like); and U.S. Pat. No. 7,842,725 (linear PEG 8-PEG-12 dimethicones having foam heights greater than 20 mm). Dimethicone copolymers, such as PEG/PPG 18/18, 17/18, 4112, 35/65, among others, are disclosed in U.S. Publication No. 2009/0326076; and derivatized dimethicones, such as PEG-8-12 dimethicones coupled with foam strengthening agents are disclosed in U.S. Publication No. 2009/0098067.

There are disadvantages to the currently available non-aerosol alcohol foam products that are currently in the market. First, there exists a general negative perception with regard to fluorosurfactants and their persistence in the environment and overall toxicity profile. Based on this perception, some have used traditional linear silicone surfactants to achieve foam creation in alcohol systems. Though not as effective as fluorosurfactants from a foam-generation standpoint, silicone surfactants are capable of producing a moderate amount of stable foam, especially when used at fairly high concentrations (e.g., 3%-5%).

Secondly, non-aerosol alcohol foam systems are very sensitive to excipient ingredients that could normally be used to enhance other attributes, specifically moisturization and overall feel. Alcohol sanitizers, due to the high level of alcohol required for acceptable microbial efficacy, can be inherently drying to the skin. Standard alcohol gels or liquids often contain water-insoluble, but alcohol soluble (or miscible) ingredients (such as occlusive agents) to improve overall moisturization benefits. However, due to the complex foam structure of alcohol-water mixtures, these ingredients often have a very significant negative impact on foam generation, quality and stability. Hence, ingredient selection may be limited.

The potential limitation for ingredient selection can also impact the microbial efficacy of the system. Though high levels of alcohol have good immediate efficacy against a broad range of microorganisms, due to its volatile nature, little prolonged microbial activity can be achieved without the addition of ingredients that either help retard the evaporation rate and/or bind to the skin. However, most ingredients traditionally used for this (e.g., cellulosic thickeners, high molecular weight occlusive agents) cannot be used in non-aerosol foam products.

As is evident from the foregoing, many non-aerosol alcohol foam systems have poor moisturization properties and/or limited microbial efficacy. While U.S. Pat. Nos. 7,268,165 and 7,985,773 to Greten et al. describe compositions that have enhanced and prolonged microbial efficacy and excellent moisturization properties, the compositions also contain thickeners that are not conducive to non-aerosol foam production.

In a healthcare environment, the CDC Guidelines for Hand Hygiene in Health Care Settings include recommendations for increased use of alcohol-based sanitizing products and, at the same time, express significant concern with skin health issues resulting from their use. Alcohol-based sanitizing products are often used on hands that do not have a visible organic load, however, many currently available products are negatively impacted by both the presence of any organic load, even that not clearly visible, and dilution. In order to leverage the CDC guidelines properly and provide a product that also has enhanced moisturization capabilities that are equivalent or superior to current alcohol-based foam sanitizers, an alcohol based foam sanitizer having efficacy and enhanced skin care properties in the presence of organic load and on repeated application is needed.

Further, the Tentative Final Monograph for Health-Care Antiseptic Drug Products sets forth the FDA criteria necessary to make the claim of "Healthcare Personnel Handwash." It is believed that when the tentative monograph issues as a final version, the criteria outlined in the tentative version will remain. For example, the Healthcare Personnel Handwash Test outlined in the tentative monograph establishes criteria that require a 2 log (base 10) reduction in bacteria after the first application and a 3 log reduction in bacteria after the tenth application. Because of the high inoculums and organic load present in the required methodology, not all alcohol-based sanitizing products can meet these criteria, especially after the tenth application and in fact, may actually demonstrate a decrease in log reduction when compared to the first application. Indeed, alcohol gel products used alone were not considered as good, from both an overall microorganism reduction profile and skin irritation potential, as a combination of alcohol gel with either an antimicrobial or a plain lotion soap. Paulson at al, *Am. J. Infect Control* 1999; 27(4): 332-38. Combination regimens may, therefore, be preferred to achieve persistent antimicrobial properties that are required by FDA criteria.

There is a need, therefore, for non-aerosol, alcohol-based hand sanitizing foam products having enhanced and prolonged antimicrobial activity, tolerance to organic load and dilution, excellent residual activity, skin moisturization and aesthetic skin feel properties, while at the same time meeting all of the CDC and FDA requirements.

A novel non-aerosol alcohol foam sanitizer has been discovered that resolves the disadvantages of current alcohol-based foam sanitizers and that will meet and exceed the criteria for a Healthcare Personnel Handwash claim. The invention is a non-aerosol alcohol foam hand sanitizer that comprises a novel silicone-dimer reaction product which, in combination with known components, resolves several issues encountered with alcohol-based sanitizing products in the past.

The inventive composition provides both the necessary surface tension reduction to allow a high alcohol system to foam without the use of propellants and aids in improving moisturization and aesthetic skin feel properties of the final product. The system contains certain ingredients previously known to enhance and prolong antimicrobial efficacy in combination with moisturizing components, but also contains novel components, not used heretofore, that provide unexpectedly high-quality, stable foam and excellent moisturizing and skin feel properties over current commercially available products.

Specifically, the inventive composition contains a high level of an aliphatic alcohol, a silicone based surfactant system comprising a novel silicone dimer reaction product, i.e., bis-PEG-10 dimethicone/dimer dilinoleate, PEG-17 dimethicone, or mixtures of both; activity enhancing substances, including an aromatic alcohol, a cationic substrate binding component, or mixtures thereof; a polyquaternium component; a blend of humectant ingredients; a cationic surfactant(s); and water-soluble emollient ingredients, all in an aqueous base. The composition is efficacious against a broad range of microorganisms, including gram-negative organisms. Importantly, the composition meets the Healthcare Personnel Flandwash guidelines at both one and ten applications, based on the criteria set forth in the Tentative Final Monograph for Health-Care Antiseptic Drug Products (1994, 21 CFR Parts 333 and 369).

The final inventive corn positions have unexpectedly superior moisturization and aesthetic feel characteristics, making it more likely that they will be used multiple times throughout the course of the day. The aesthetics of the inventive composition are such that the rub-in time, residue and foam properties are similar to current commercially available non-aerosol alcohol-based foam products, but with superior after-feel properties.

It is an object of the invention to provide a non-aerosol, foaming alcohol-based hand sanitizer product, having excellent moisturization and aesthetic skin-feel properties, while still producing a large amount of quality foam that is stable even in the presence of high amounts of alcohol.

It is yet another object of the invention to provide a non-aerosol, foaming alcohol-based hand sanitizer product having enhanced and prolonged antimicrobial activity against a broad range of microorganisms, including gram negative organisms, that is, at minimum, equivalent, but in many instances superior, to the antimicrobial activity of currently available non-aerosol, foaming alcohol-based hand sanitizers.

It is a further object of the invention to provide a non-aerosol, foaming alcohol-based hand sanitizer product that has superior tolerance for organic load and dilution, even with repeated applications, and excellent residual activity as compared to currently marketed non-aerosol, foaming alcohol-based hand sanitizers.

It is a further object of the invention to provide a non-aerosol, foaming alcohol-based hand sanitizer that is environmentally friendly, free of fluorosurfactants and that meets CDC guidelines and FDA criteria for hand sanitizing compositions.

SUMMARY OF THE INVENTION

The novel inventive compositions combine known and novel components to achieve a non-aerosol, high-alcohol-containing foam hand sanitizer that has excellent antimicrobial properties, with tolerance for organic load and dilution, excellent residual activity, and superior skin conditioning (moisturizing, aesthetic skin-feel) characteristics. The composition comprises: an aliphatic alcohol; a silicone based surfactant; an aromatic alcohol as an activity enhancing substance; a cationic substrate binding activity enhancing substance; a polyquaternium; a humectant; a cationic surfactant; an emollient; and water. More than one of each type of component may be utilized within the scope of the invention.

DETAILED DESCRIPTION OF THE INVENTION

Figure 1:
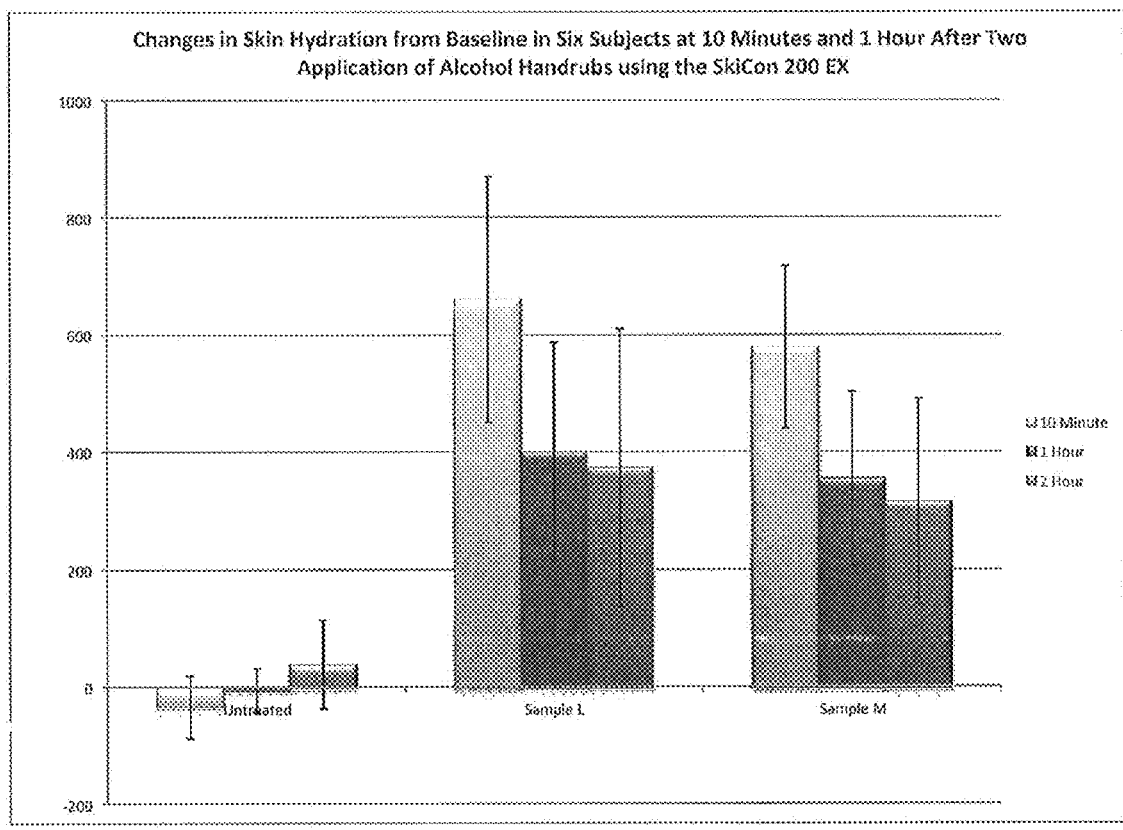
FIG. 1 is a chart demonstrating Skicon Measurements reflecting moisturization characteristics of the inventive compositions.

The novel inventive compositions of the invention meet and exceed criteria for a Healthcare Personnel Handwash claim as promulgated by the FDA. The invention provides a non-aerosol, foaming high alcohol content hand sanitizing composition with excellent antimicrobial and skin conditioning properties without the disadvantages of currently marketed hand sanitizers.

The antimicrobial activity of the present inventive compositions are the result of combining high amounts of an aliphatic alcohol, a preservative having known gram-negative activity, and emollients that have antimicrobial activity of a persistent nature. The superior moisturization characteristics are the result of the addition of known humectants, skin feel agents, and skin conditioners, and surfactants.

The key to a non-aerosol foaming alcohol-based hand sanitizer is the amount, quality and stability of the foam produced. Skin conditioning agents, while desirable and necessary, often affect the amount and quality of the foam or its stability. A key material in the generation and stability of foam in the inventive compositions is a new silicone surfactant, which is a polyester made by the reaction of dimer acid and PEG-10 dimethicone. Alternatively, another dimethicone surfactant, PEG-17 dimethicone, has been found to produce unexpectedly large amounts of quality foam with excellent stability. These surfactants, in combination with the other components of the inventive compositions, eliminate the need for foam strengthening agents or separate stabilizing agents that are required in current commercial products.

Preferred embodiments of the inventive compositions include: an aliphatic alcohol in amounts ranging from about 50 to about 60 wt. %; a silicone-based surfactant in amounts ranging from about 1 to about 5 wt. %; an activity enhancing component that is an aromatic alcohol or a cationic substrate binding component, or both; skin conditioning agents, such as polyquaternium compounds, humectants; a cationic surfactant; emollients and water. Each type of component may be present as a mixture of one or more components of that type.

The aliphatic alcohol is an active ingredient for the formulation. The alcohol has from 1 to 8 carbon atoms. This component is recognized by the FDA as an antimicrobial ingredient. Ethanol is a preferred aliphatic alcohol for the inventive compositions. Ethanol, when used, is 200 proof, and may be Specifically Denatured Alcohol (SDA) 40-B, which utilizes both tert-butyl alcohol (0.12%) and denatonium benzoate (0.0006%) as denaturants. Another appropriate alcohol is SDA 40-2, which utilizes both tea-butyl alcohol (0.12%) and brucine sulfate (0.014%). Other SDA alcohols are known to one skilled in the art and are within the scope of this invention. Ethanol has broad spectrum activity against bacteria and some viruses and evaporates on rub-in. As such, ethanol is highly preferred, but other alcohols, including but not limited to butyl, n-propyl and isopropyl alcohol may also be used.

The aliphatic alcohol is present in amounts greater than about 40 wt. % up to about 85 wt. %; optimally, greater than about 50 wt. % and less than about 70 wt. %, based upon the total weight of the components of the inventive compositions. Preferable ranges are 50-60 wt. %.

The silicone-based surfactant component is primarily responsible for generating foam in the inventive compositions; however, the surfactants of the present invention surprisingly also add to the aesthetic feel of the product. An unexpectedly large amount of quality, stable foam is generated, even in view of the several skin conditioning/feel agents included in the composition. Preferably, the surfactant comprises bis-PEG-10 dimethicone/dimer dilinoleate, a dimer reaction product. This novel component is provided under the trade name ZENESTER ME (Zenitech LLC). Another acceptable silicone-based surfactant is PEG-17 dimethicone, which also produces an unexpectedly large amount of good quality, stable foam in the inventive compositions. This material is provided under the trade name SILSOFT 895 (Momentive Performance Materials, Inc.)

The silicone-based surfactant component is present in amounts of from about 1.0 wt % to about 3.0 wt. %, based upon the total weight of the components of the inventive composition. The silicone-based surfactant component may be a mixture of the novel bis-PEG-10 dimethicone/dimer dilinoleate or PEG-17 dimethicone.

The aromatic alcohol comprises phenoxyethanol, also known as ethylene glycol monophenyl ether. It is used as a preservative and provides activity against Gram-negative organism. It is combined in the inventive compositions with other components having antimicrobial activity yielding a broad range of coverage for the inventive compositions. Other suitable aromatic alcohols include benzyl alcohol and 1-phenoxy-2-propanol.

The aromatic alcohol is present in amounts greater than about 0.1 wt % up to about 5.0 wt. %; optimally, greater than about 0.5 wt. % up to about 3.0 wt. %, based upon the total weight of the components of the inventive composition.

The cationic substrate binding activity enhancing substance is behentrimonium methosulfate. This emollient is a quaternary ammonium salt derived from Rapeseed Oil. Its $C_{22}$ chain length and cationic charge make it substantive to the skin and provide a smooth after-feel that is aesthetically pleasing to the user. It has some antimicrobial activity as well. Other acceptable cationic substrate binding activity enhancing substances include without limitation behenalkonium chloride, behentrimonium chloride, behenoyl PG-trimonium chloride and behenamidopropyl PG-dimonium chloride.

The cationic substrate binding, activity enhancing substance is present in amounts greater than about 0.01 wt. % up to about 1.0 wt. %, optimally greater than about 0.05 wt % up to about 0.5 wt. %, based upon the total weight of the components in the system.

The polyquaternium ingredient preferably comprises polyquaternium-6. This component is a cationic polymer which acts as a skin conditioner. It is the quaternary ammonium salt of acrylamide and dimethyl diallyl ammonium chloride monomers. It aids lubricity while rubbing onto the skin and contributes a soft after-feel. Other suitable polyquaternium materials include polyquaternium-7.

The polyquaternium component is present in amounts of about 0.1 wt. % up to about 2.0 wt. %, optimally, about 0.1 wt. % to about 1.0 wt. %, based upon the total weight of the components of the inventive composition.

The humectant in the inventive compositions preferably comprises glycerin, a well-known humectant that results in significant impact on moisturization properties of the inventive compositions, even when used at ow levels. Another suitable humectant is 2-methyl-1,3-propanediol, which is both a solvent and a humectant. The humectants can be used separately, or in combination. In particular, 2-methyl-1,3-propanediol provides additional humectant properties, while reducing the tacky feel associated with glycerin, so that the combination of these two humectants is desirable. Other humectants useful in the inventive compositions include propylene glycol, ethylene glycol, butylene glycol, triethylene glycol, diethylene glycol, dipropylene glycol, tripropylene glycol, hexylene glycol, sorbitol, dimethyl isosorbide, sodium PCA, and hydrolyzed corn starch hydroxyethyl ether. Other humectants suitable in the present inventive compositions are known to one skilled in the art.

The humectant component(s) are present in total amounts of about 0.1 wt. % up to about 10.0 wt. %, optimally, about 1.5 wt. % up to about 3.0 wt. %, based upon the total weight of the components of the inventive composition.

The cationic surfactant comprises cocamidopropyl PG-dimonium chloride phosphate (known as ARLASILK PTC (Croda)) a quaternary ammonium salt derived from coconut oil. Although it is classified as a surfactant, it provides additional skin conditioning properties to the inventive compositions and aids in stabilizing the foam generated by the silicone-based surfactants upon dispensing, eliminating the need for additional foam stabilizing agents. Other suitable options include sodium coco PG-dimonium chloride, myristamidopropyl PG-dimonium chloride phosphate, linoleamidopropyl PG-dimonium chloride phosphate, and stearamidopropyl PG-dimonium chloride phosphate.

The cationic surfactant is present in amounts of about 0.1 wt. % to 5.0 wt. %, optimally, about 1.0 wt. % to about 3.0 wt. %, based upon the total weight of the components in the system.

Emollient ingredients may include, but are not limited to, PEG-45 palm kernel glycerides, cetyl lactate, $C_{12-15}$ alkyl benzoate, and PEG-7 glyceryl cocoate. Other emollients are known to those skilled in the art and include but are not limited to cetyl myristate, glyceryl dioleate, isopropyl myristate, lanolin, methyl laurate, PPG-9 laurate, octyl palmitate, PPG-5 lanoate, and di-PPG-3 myristyl ether adipate. These emollients are skin conditioning agents that help improve rub-in characteristics and aid in the after-feel aesthetics. A combination of emollients may be used.

Emollients are present in total amounts of about 0.01 wt. % up to about 5.0 wt. %, optimally, about 0.01 wt % up to about 3.0 wt. %, based upon the total weight of the components of the inventive compositions.

The balance of the inventive composition is water. Use of deionized water is necessary for the inventive compositions and should have a relatively low bioburden to maintain preservative effectiveness.

The novel combination of components offers significant advantages over prior art compositions in that they provide superior foaming characteristics, without the use of aerosols or fluorosurfactants, both of which have negative environmental and toxicity profiles. The compositions also provide superior antimicrobial efficacy, both immediate and prolonged, against a wide range of microbes, including but not limited to gram-negative bacteria. The inventive compositions possess superior moisturizing characteristics and do not require the use of a fragrance.

Generally, the inventive compositions may be prepared by simple mixing of components. One exemplary process for preparing one embodiment of the inventive compositions is set forth below:

| Raw Material | Process |
| --- | --- |
| Deionized Water | Charge water. |
| Behentrimonium methosulfate | Add with mixing to cold water |
| | Begin heating to 76° C. (169° F.) to melt/dissolve the G073 into water. Once temperature is reached, turn off heat source, and cool to a target of 35° C. (95° F.). Once temperature of the batch reaches 35° C. (95° F.), continue. |
| Polyquaternium-6 | Add with mixing. |
| Glycerin | Add with mixing. |
| Methylpropanediol | Add with mixing. |
| Phenoxyethanol | Add with mixing. |
| Cocamidopropyl PG-dimonium chloride phosphate | Add with mixing. |
| PEG-7 glyceryl cocoate | Add with mixing. |
| PEG-45 palm kernel glycerides | Add with mixing. |
| Bis-PEG-10 dimethicone/dimer dilinoleate | Add with mixing. |
| Deionized Water | Charge water (used to q.s. batch) |
| Ethanol, 200 proof, SDA 40-B | Add with mixing (all normal precautions and equipment used to hand flammable materials must be followed). |

As is clear from the above, the behentrimonium methosulfate is a solid material, and thus, it must be added at a high temperature, so it can melt into the system. After it has melted, other components facilitate bringing it into solution as they are added. The other components can be added in any order (once the batch has cooled to the appropriate temperature), except for the alcohol, which is added last, because it is volatile.

The invention is further described by the examples below.

EXAMPLES

Example 1

Foam Quality and Stability

A number of different components were screened to evaluate their ability to create a stable foam in a 70% w/w ethanol solution (aqueous). For this evaluation, approximately one gram of each component was added to 15 grams of the ethanol solution in a vial. The vial was shaken by hand for 15 seconds, then the foam profile was evaluated using the following evaluation scale:

Poor—little to no foam generated
Moderate—some foam generated, and/or foam generated collapsed rapidly
Good—large amount of foam was generated and foam was stable (did not collapse rapidly)

The results of the foam testing are shown in Table 1, below:

TABLE 1

| Raw Material | Foam Profile |
|---|---|
| Sodium Lauroyl Lactylate | Poor |
| Hydrolyzed Corn Starch | Moderate |
| Phenoxyethanol | Poor |
| Glycerin | Poor |
| Glycereth-18 Ethylhexanoate | Moderate |
| PPG-12 SMDI Copolymer | Moderate |
| PEG-8 SMDI Copolymer | Moderate |
| Polyquaternium-37 | Poor |
| Cocamidopropyl Betaine and Sodium Lauroyl Lactylate | Poor |
| Potassium Lauroyl Wheat Amino Acids | Poor |
| Alkyl Glucoside | Poor |
| Lauramine Oxide | Poor |
| POE-2 Coco Amine | Poor |
| Olealkonium chloride | Poor |
| Stearamidopropyl dimethylamine lactate | Poor |
| Quaternium-26 | Poor |
| Quaternium-92 | Poor |
| Isostearamidopropyl Morpholine Lactate | Poor |
| Didecyl dimethyl ammonium chloride | Poor |
| Bis-PEG-10 Dimethicone/Dimer Dilinoleate | Good |
| Hydroxypropyl Guar | Poor |
| Myristamidopropyl PG-dimonium chloride | Poor |
| Cocamidopropyl PG-Dimonium Chloride Phosphate | Poor |
| Behentrimonium Methosulfate | Poor |
| PPG-15 Stearyl Ether | Poor |
| Dimethyl Isosorbide | Poor |
| Glycereth-7 Cocoate | Poor |
| Isosteareth-3 Octanoate | Poor |
| Sodium Lauroyl Sarcosinate | Poor |
| Lecithin | Poor |
| Amodimethicone | Poor |
| PEG-17 Dimethicone | Good |
| Behenyl Dimethicone | Poor |

The results obtained show that, the surfactants used in the inventive compositions provided superior foam generation and stability compared to other components known and available for use.

Example 2

Moisturization/Hydration Studies

Several different iterations of the inventive compositions are shown below in Table 2.

TABLE 2

| Ingredient | A | B | C | D | E | F | G | H | I | J | K | L | M |
|---|---|---|---|---|---|---|---|---|---|---|---|---|---|
| Deionized Water | 36.10 | 37.41 | 38.21 | 36.53 | 36.85 | 37.00 | 35.74 | 37.25 | 34.22 | 34.76 | 34.60 | 36.10 | 37.00 |
| Behentrimonium Methosulfate | 0.10 | 0.10 | 0.19 | 0.20 | 0.10 | 0.10 | 0.10 | 0.20 | | | 0.20 | 0.10 | 0.10 |
| Behenalkonium Chloride | | | | | | | | | | 0.2 | | | |
| Glycerin | 0.75 | 0.50 | 0.47 | 0.49 | | 0.35 | 0.51 | 0.53 | 0.42 | 0.5 | 0.66 | 0.75 | 0.35 |
| Polyquaternium-6 | 0.50 | 0.55 | 0.49 | 0.49 | 0.50 | 0.50 | 0.50 | 0.57 | 0.53 | 0.51 | 0.52 | 0.50 | 0.50 |
| Tridecyl Nonanoate | | | | | | | | | 0.25 | | | | |
| Poloxamer 188 | | | 0.45 | 0.50 | | | | | | | 0.49 | 0.49 | |
| Hydroxypropyl Cellulose | | | | | | | | 0.24 | | | | | |
| Cetyl Lactate | | 0.50 | | | | | 0.20 | 0.52 | 0.76 | | | | |
| PEG-17 Dimethicone | | | 2.67 | 2.99 | | | 2.00 | | | 3.04 | 2.98 | | |
| Methylpropanediol | 2.00 | 2.05 | 1.77 | 2.11 | 2.00 | 1.50 | 2.00 | 2.00 | 2.01 | 2 | 2.03 | 2.00 | 1.50 |
| Phenoxyethanol | 1.25 | 1.24 | 1.16 | | 1.25 | 1.25 | 1.25 | 2.06 | 1.25 | 1.25 | 1.26 | 1.25 | 1.25 |
| Cocamidopropyl PG-Dimonium chloride phosphate | 1.50 | 1.00 | 0.45 | 0.49 | 1.50 | 1.50 | 1.50 | | 1.77 | 0.52 | 0.51 | 1.60 | 1.50 |
| PEG-45 Palm Kernel Glycerides | 0.10 | | | | 0.10 | 0.20 | | | 0.52 | | | 0.10 | 0.10 |
| PEG-7 Glyceryl Cocoate | 0.50 | | | | 0.50 | 0.40 | | | | | | 0.50 | 0.50 |
| Bis-PEG-10 Dimethicone/Dimer Dilinoleate | 2.00 | 1.50 | | | 2.00 | 2.00 | 1.00 | 1.49 | 1.55 | | | 2.00 | 2.00 |
| Ethyl Alcohol (SDA-40-B 200 Proof) | 55.20 | 55.15 | 54.15 | 56.21 | 55.20 | 55.20 | 55.20 | 55.14 | 56.72 | 56.73 | 56.75 | 55.20 | 55.20 |

Two samples of inventive formulations (L and M from Table 2) were tested in a moisturization study. In the study, six subjects used IVORY bar soap to wash the test site (volar forearm) for one minute. After the wash with IVORY soap, the test site was allowed to equilibrate for 30 minutes. After equilibration, Skicon measurements were taken as a baseline. (Skicon measurements are conductance-based measurements in which conductance is used to determine the hydration levels of the skin.) Test product was then applied on a randomized test site on the forearm, and Skicon measurements were taken at specific time-points after product application. The results in FIG. 1 showed that both samples achieved a significant improvement in skin hydration at all time-points evaluated versus the untreated control.

Additional testing was done to measure relative hydration of the skin after 1 hour, using a NOVA DPM 9003 ("NOVA")

Figure 3:
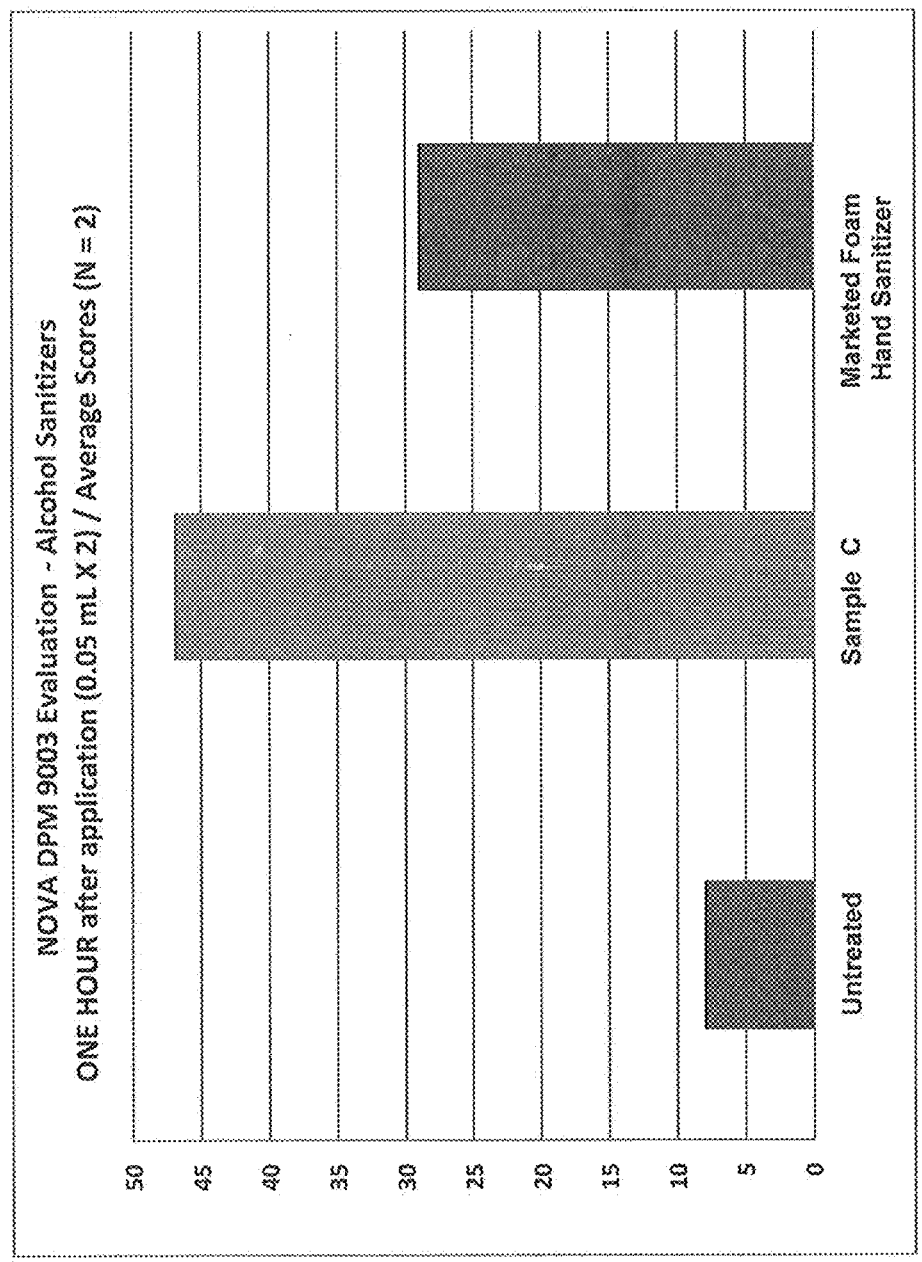
FIG. 3 is a chart demonstrating superior moisturization properties of an inventive composition (C) as compared to an untreated control and an existing marketed product, using a NOVA DPM 9003 instrument, which measures relative hydration of the skin.

Evaluation of the inventive composition as compared to a currently available, commercial alcohol-based hand sanitizer foam. The NOVA Evaluation is an impedance-based conductance measurement of the hydration of the skin, which is similar to the Skicon test described above, but the mechanics of instrument used are slightly different. Higher values mean better hydration of the skin. Results in FIG. 3 showed that the inventive composition was significantly better in hydrating the skin than the current commercial product.

Example 3

Antimicrobial Efficacy-HCPHW

Figure 2:
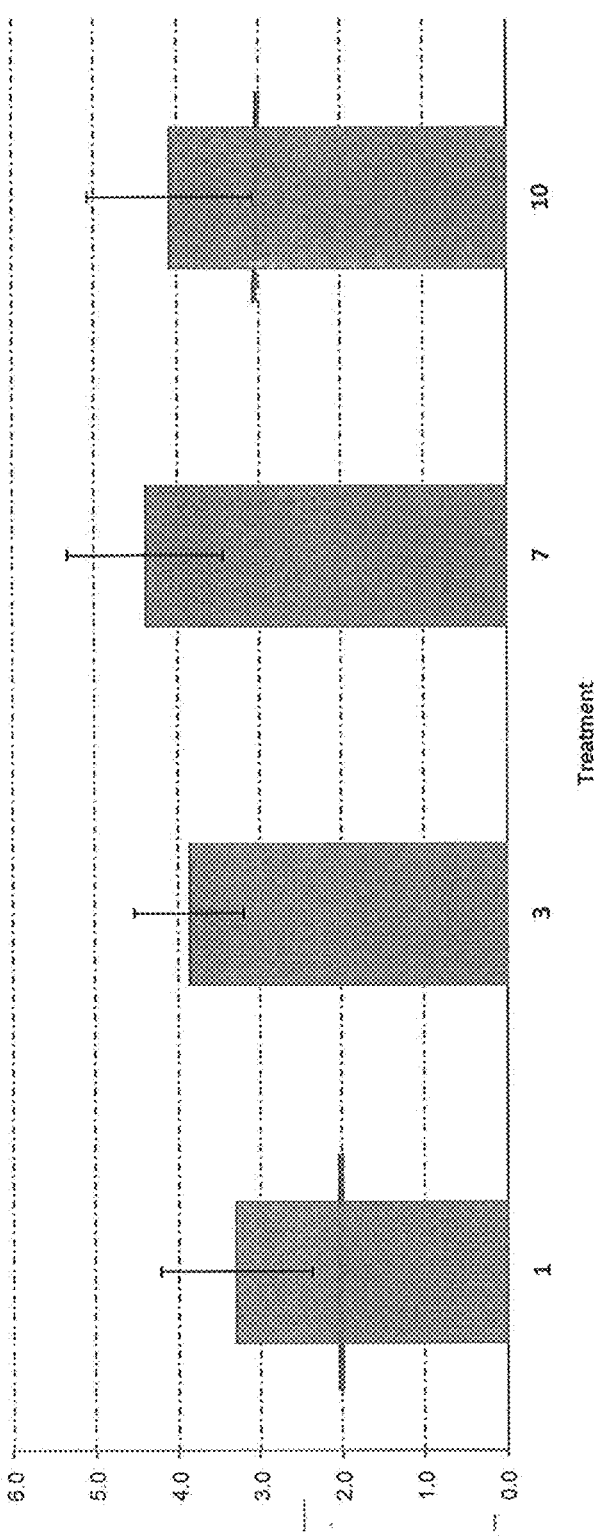
FIG. 2 is a chart demonstrating Healthcare Personal Handwash efficacy of an inventive composition (F) and showing an increased average log reduction as the number of applications of the composition increases.

A Healthcare Personnel Hand Wash study was done to evaluate the efficacy of the inventive composition using the challenge organism *Serratia marcescens* 14756. *S. marcescens* is a marker microorganism often used in testing because it produces a characteristic red colony that is easily distinguishable from normal microbial populations of the hands, as well as from other contaminating organisms. Results in FIG. 2 showed significant average log reductions in twelve subjects, which increased with increasing numbers of applications.

Example 4

Antimicrobial Efficacy

Residual Activity Testing

In yet another study, four samples were compared to evaluate whether the inventive compositions achieved a greater log reduction than plain ethanol solutions. Two of the samples contained ethanol alone at concentrations of 62% w/w (N) and 70% w/w (O). The other two samples were inventive compositions/formulations, one having 62% w/w (P) and the other having 70% w/w ethanol (Q) along with the other components of the inventive compositions. The components of each sample are set forth in Table 3 below.

TABLE 3

|  | Sample N | Sample O | Sample P | Sample Q |
|---|---|---|---|---|
| Deionized Water | 38.00 | 30.00 | 30.65 | 22.68 |
| Ethanol | 62.00 | 70.00 | 62.0 | 70.0 |
| PEG-17 dimethicone |  |  | 2.07 | 2.07 |
| Glycerin |  |  | 0.68 | 0.62 |
| Phenoxyethanol |  |  | 2.50 | 2.50 |
| Methylpropanediol |  |  | 1.51 | 1.52 |
| Polyquaternium-6 |  |  | 0.48 | 0.49 |
| Behentrimonium Methosulate |  |  | 0.11 | 0.12 |

Each sample was evaluated at two different inoculation/treatment cycles, i.e., at 1 inoculation/treatment and 5 inoculations/treatments. Tests were completed using the pigskin model, the inoculant, *Serratia marcescens*, and 1 and 5 inoculation/treatment cycles. The "pigskin model" is a method designed to simulate a HCPHW test using pigskins prepared according to the method described in U.S. Pat. No. 7,985,773 to Greten et al., incorporated herein by reference.

In this example, pigskin pairs were inoculated with bacteria, rubbed together for 15 seconds, and allowed to air dry for 1 minute. The two different ethanol solutions having concentrations of 62% w/w and 70% w/w and two different product formulations N and O, one having 62% w/w ethanol (N) and the other having 70% w/w ethanol (O), were applied to pairs of pigskins (0.2 ml per pair/0.1 ml per piece). The pairs of pigskins (having the same treatment) were rubbed together for 30 seconds and allowed to air dry for 4 minutes. Neutralizer was then applied to the pigskins, they were debrided for 30 seconds, serially diluted and plated.

Figure 4:
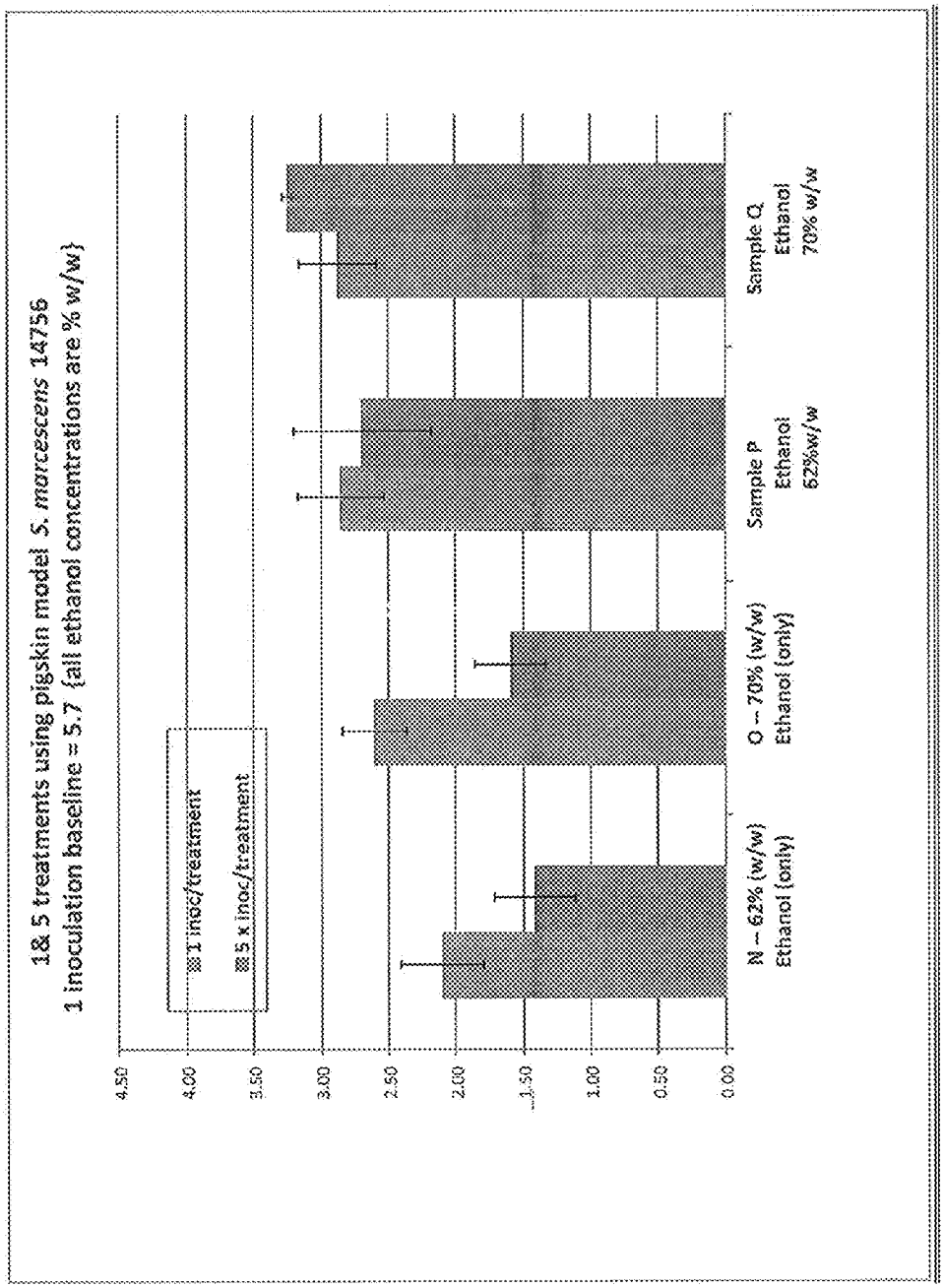
FIG. 4 is a chart reflecting results obtained using a pigskin model and an inoculant, *Serratia marcescens*, comparing two ethanol solutions at two different concentrations (N, O) with two inventive formulations having the same ethanol concentrations (P, Q) and demonstrating superior log reductions obtained with the inventive formulations compared to ethanol alone at 1 and 5 inoculation/treatment cycles.

Results are shown in FIG. 4 and show significant log reductions. FIG. 4 shows that by adding other components of the formulation, such as the activity enhancing substances, efficacy was enhanced over simply using ethanol at the same concentration. The enhancement was seen at 1 application (inoculation/treatment cycle), but was more pronounced at 5 applications, showing excellent tolerance for organic load and dilution with inoculum. The data showed that ethanol alone did provide efficacy upon initial treatment, but the efficacy decreased upon multiple treatments due to the organic load. However, the two formulated systems (P and Q), which contained additional components of the inventive compositions maintained or increased the log-reduction (efficacy) at the fifth application.

In yet another study, the residual activity of an inventive composition (R) was compared to a commercially available alcohol-based product using a pigskin model and a 5-application (5 treatments of the inventive composition R and marketed product; alcohol allowed to dry prior to inoculation). Formula R is set forth in Table 4, below:

TABLE 4

| Component | R (wt. %) |
|---|---|
| Deionized Water | 34.74 |
| Ethanol | 56.73 |
| PEG-17 dimethicone | 3.04 |
| Glycerin | 0.50 |
| Phenoxyethanol | 1.25 |
| Methylpropanediol | 2.00 |
| Poloxamer 188 | 0.49 |
| Cocamidopropyl PG-dimonium chloride phosphate | 0.52 |
| Polyquaternium-6 | 0.51 |
| Behenalkonium chloride | 0.20 |

Figure 5:
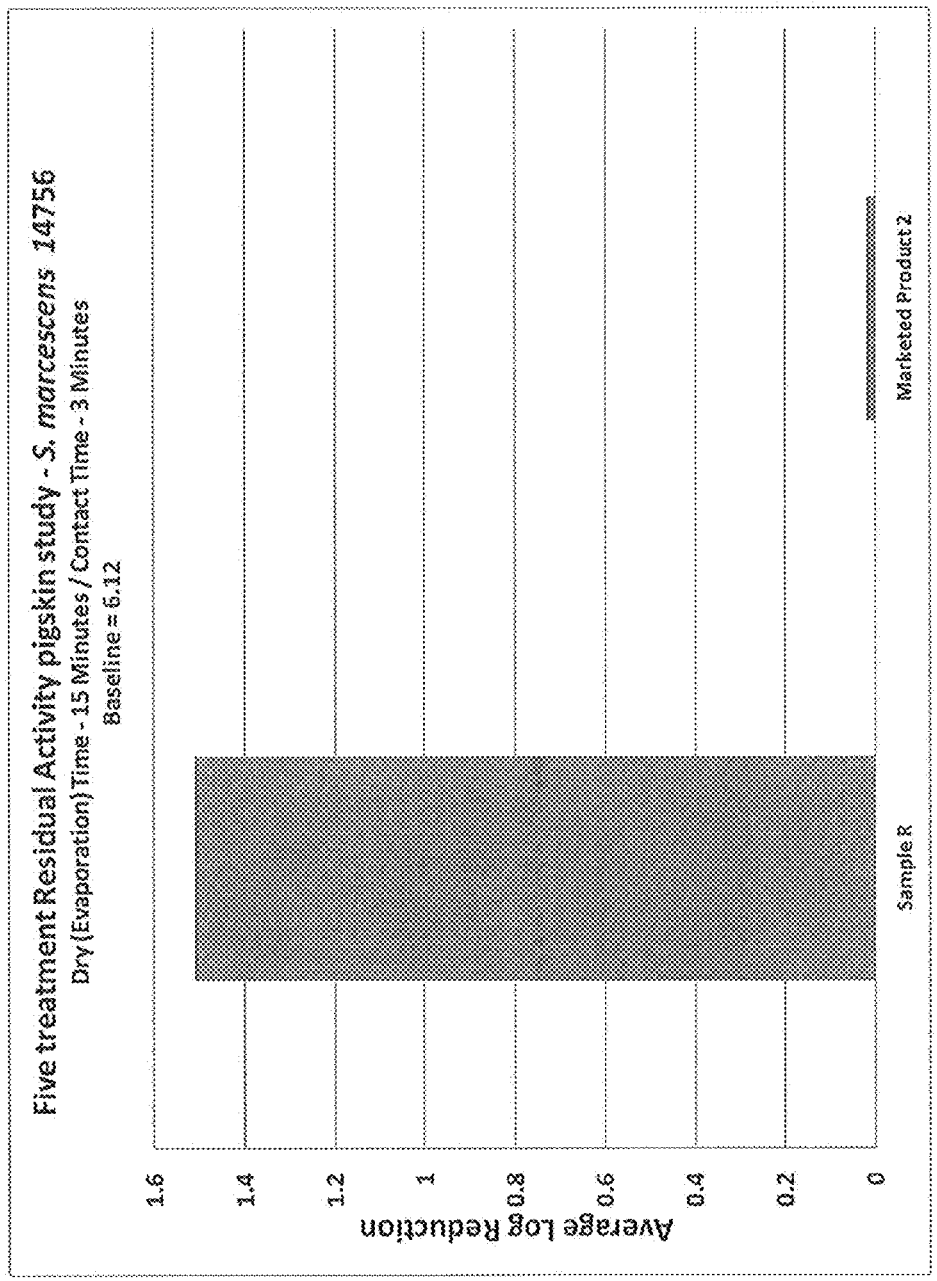
FIG. 5 is a chart reflecting results obtained using a 5-application (inoculation/treatment cycle) pigskin test, comparing an inventive composition (R) with a leading commercial sanitizing product and demonstrating superior efficacy and residual activity of the inventive formulation as compared to a commercial product.

Results in FIG. 5 showed that at a 5-application pigskin study, a leading commercially available alcohol-based hand sanitizing foam product had almost no activity, whereas the inventive composition had a 1.5-log reduction, which for this type of pigskin study is expected for a good product that will stand up to organic load and dilution and result in a formulation that will pass FDA criteria for 10 applications in a Healthcare Personnel Handwash test.

This invention includes the use of a novel silicone surfactant that not only helps generate foam in a system with high amounts of alcohol, but also adds to the overall aesthetic feel and moisturization of the system. The addition of other ingredients (phenoxyethanol, behentrimonium methosulfate and poiyquaternium-6) provides a system that exceeds the FDA's Tentative Final Monograph requirements for Healthcare Personnel Handwash efficacy. The inventive composition(s) show excellent tolerance for organic load and dilution and have excellent residual activity. The enhanced emollient system also provides moisturization to the user for hours after application, keeping the skin hydrated.

In accordance with the patent statutes, the best mode and preferred embodiment have been set forth; the scope of the invention is not limited thereto, but rather by the scope of the attached claims.

What is claimed is:

1. A non-aerosol, foaming sanitizing composition having enhanced and prolonged antimicrobial activity, consisting of:
   a. an aliphatic alcohol consisting of ethanol, butyl alcohol, n-propyl alcohol, or isopropyl alcohol, or mixtures thereof, present in amounts ranging from about 40 wt. % up to about 85 wt. %;

b. an activity-enhancing substance consisting of (i) an aromatic alcohol consisting of phenoxyethanol, benzyl alcohol, or 1-phenoxy-2-propanol, or mixtures thereof, present in amounts ranging from about 0.1 wt. % to about 5 wt. %, or (ii) a cationic substrate binding activity-enhancing substance consisting of behentrimonium methosulfate, behenalkonium chloride, behentrimonium chloride, behenoyl PG-trimonium chloride, or behenamidopropyl PG-dimonium chloride, or mixtures thereof, present in amounts ranging from about 0.01 wt. % up to about 1 wt. %, or (iii) mixtures of both;

c. a silicone-based surfactant consisting of bis-PEG-10 dimethicone/dimer dilinoleate, present in amounts ranging from about 1.0 wt. % to about 3.0 wt. %;

d. a polyquaternium compound present in amounts ranging from about 0.1 wt. % to about 2.0 wt. %;

e. a humectant present in amounts ranging from about 0.1 wt. % up to about 10 wt. %;

f. a cationic surfactant present in amounts ranging from about 0.1 wt. % to about 5.0 wt. %;

g. an emollient present in amounts ranging from about 0.01 wt. % up to about 3.0 wt. %; and h. water, wherein the composition has excellent tolerance for organic load and dilution and excellent residual antimicrobial activity.

2. The composition set forth in claim 1, wherein the polyquaternium is polyquaternium-6 or polyquaternium-7, or mixtures thereof; wherein the humectant is glycerin, 2-methyl-1,3-propanediol, propylene glycol, ethylene glycol, butylene glycol, triethylene glycol, dipropylene glycol, tripropylene glycol, hexylene glycol, sorbitol, dimethyl isosorbide, sodium PCA, or hydrolyzed corn starch hydroxyethyl ether, or mixtures thereof; wherein the cationic surfactant is cocamidopropyl PG-dimonium chloride phosphate, coco PG-dimonium chloride, myristamidopropyl PG-dimonium chloride phosphate, linoleamidopropyl PG-dimonium chloride phosphate, or stearamidopropyl PG-dimonium chloride phosphate, or mixtures thereof; and wherein the emollient is PEG-45 palm kernel glycerides, cetyl lactate, C12-C15 alkyl benzoates, PEG-7 glyceryl cocoate, cetyl myristate, glyceryl dioleate, isopropyl myristate, lanolin, methyl laurate, PPG-9 laurate, octyl palmitate, PPG-5 lanoate, or di-PPG-3 myristyl ether adipate, or mixtures thereof.

3. The composition as set forth in claim 1, wherein the aliphatic alcohol is ethanol.

4. The composition as set forth in claim 1, wherein the aliphatic alcohol is present in amounts ranging from about 50 wt. % up to about 70 wt. %; wherein the aromatic alcohol is present in amounts ranging from about 0.5 wt. % up to about 3 wt. %; wherein the cationic substrate binding component is present in amounts ranging from about 0.05 wt. % up to about 0.5 wt. %; wherein the polyquaternium compound is present in amounts ranging from about 0.1 wt. % up to about 1 wt. %; wherein the humectant is present in amounts ranging from about 1.5 wt. % up to about 3.0 wt. %; wherein the cationic surfactant is present in amounts of about 1.0 wt. % up to about 3.0 wt. %; and wherein the emollient is present in an amounts ranging from about 0.01 wt. % up to about 3.0 wt. %, based upon the total weight of the components in the composition.

5. A non-aerosol, foam sanitizing composition, having enhanced and prolonged antimicrobial activity, consisting of:

a. ethanol present in an amount ranging from about 50 wt. % to about 60 wt. %;

b. a silicone-based surfactant consisting of bis-PEG-10 dimethicone/dimer dilinoleate, present in a total amount ranging from about 1 wt. % to about 3 wt. %;

c. an aromatic alcohol consisting of phenoxyethanol, benzyl alcohol or 1-phenoxy-2-propanol, or mixtures thereof, present in a total amount ranging from about 0.5 wt. % to about 3.0 wt. %;

d. a cationic substrate binding activity-enhancing substance consisting of behentrimonium methosulfate or behenalkonium chloride, present in an amount ranging from about 0.05 wt. % to about 0.5 wt. %;

e. a polyquaternium compound consisting of polyquaternium-6 or polyquaternium-7, present in an amount ranging from about 0.1 wt. % to about 1.0 wt. %;

f. a humectant consisting of glycerin, 2-methyl-1,3-propanediol, or mixtures thereof, present in a total amount ranging from about 1.5 wt. % up to about 3.0 wt. %;

g. a cationic surfactant consisting of cocamidopropyl PG-dimonium chloride phosphate or coco PG-dimonium chloride, present in an amount ranging from about 1 wt. % up to about 3.0 wt. %;

h. an emollient consisting of PEG-45 palm kernel glycerides, cetyl lactate, $C_{12}$-$C_{15}$ alkyl benzoates, or PEG-7 glyceryl cocoate, or mixtures thereof, present in a total amount ranging from about 0.01 wt. % up to about 3.0 wt. %; and i. water up to 100 wt. %, based upon the total weight of the components of the composition.

6. A non-aerosol, foaming alcohol-based hand sanitizer, consisting of:

a. ethanol present in amounts ranging from about 50 wt. % to about 60 wt. %;

b. bis-PEG-10 dimethicone/dimer dilinoleate present in amounts ranging from about 1.0 wt. % to about 3.0 wt. %;

c. phenoxyethanol;

d. behentrimonium methosulfate;

e. polyquaternium;

f. 2 methyl-1,3-propanediol and glycerin as humectants;

g. cocamidopropyl PG-dimonium chloride phosphate;

h. PEG-45 palm kernel glycerides and PEG-7 glyceryl cocoate as emollients; and i. water, wherein the composition has enhanced and prolonged antimicrobial activity, excellent tolerance for organic load and dilution, and excellent residual antimicrobial activity.

7. A non-aerosol, foaming alcohol-based hand sanitizer, consisting of:

a. ethanol present in amounts ranging from about 50 wt. % to about 60 wt. %;

b. bis-PEG-10 dimethicone/dimer dilinoleate present in amounts ranging from about 1.0 wt. % to about 3.0 wt. %;

c. phenoxyethanol;

d. behentrimonium methosulfate;

e. 2 methyl-1,3-propanediol and glycerin as humectants;

f. cocamidopropyl PG-dimonium chloride phosphate;

g. one or more emollients; and h. water, wherein the composition has enhanced and prolonged antimicrobial activity, excellent tolerance for organic load and dilution, and excellent residual antimicrobial activity.

8. A non-aerosol, foaming alcohol-based hand sanitizer, consisting of:

a. ethanol present in amounts ranging from about 50 wt. % to about 60 wt. %;

b. bis-PEG-10 dimethicone/dimer dilinoleate present in amounts ranging from about 1.0 wt. % to about 3.0 wt. %;
c. an activity-enhancing substance consisting of phenoxyethanol and behentrimonium methosulfate;
d. one or more humectants;
e. a cationic surfactant;
f. one or more emollients; and
g. water,
wherein the composition has enhanced and prolonged antimicrobial activity, excellent tolerance for organic load and dilution, and excellent residual antimicrobial activity.

* * * * *

UNITED STATES PATENT AND TRADEMARK OFFICE
CERTIFICATE OF CORRECTION

Page 1 of 1

PATENT NO. : 9,089,129 B2
APPLICATION NO. : 13/644677
DATED : July 28, 2015
INVENTOR(S) : Christopher C. Heisig and Nancy-Hope E. Kaiser It is certified that error appears in the above-identified patent and that said Letters Patent is hereby corrected as shown below:

Claims

In column 13, claim 1, line 22, please replace "3.0 wt. %" with --5.0 wt. %--

In column 14, claim 6e, line 37, please replace "polyquaternium;" with --polyquaternium 6;--

Signed and Sealed this
Twenty-ninth Day of December, 2015

Michelle K. Lee
*Director of the United States Patent and Trademark Office*